United States Patent [19]

Chalk et al.

[11] 4,266,087
[45] May 5, 1981

[54] PROCESS FOR PREPARING A MYRCENOL, CIS-OCIMENOL MIXTURE SUBSTANTIALLY FREE OF TRANS-OCIMENOL

[75] Inventors: Alan J. Chalk, Kinnelon; Steven A. Magennis, Wayne, both of N.J.

[73] Assignee: Givaudan Corporation, Clifton, N.J.

[21] Appl. No.: 960,152

[22] Filed: Nov. 13, 1978

[51] Int. Cl.$^3$ .................... C07C 29/44; C07C 29/88; C07C 29/00; C07C 33/02

[52] U.S. Cl. ................................ 568/875; 260/459 R; 260/567.6 H; 260/567.6 M; 260/583 H; 260/598; 546/184; 546/240; 546/248

[58] Field of Search ........... 568/875; 260/598, 501.15, 260/583 H, 459 R, 567.6 H, 567.6 M; 546/184, 240, 248

[56] References Cited

U.S. PATENT DOCUMENTS

| 2,871,271 | 1/1959 | Booth | 568/875 |
|---|---|---|---|
| 2,947,780 | 8/1960 | Teegarden et al. | 260/598 |
| 3,075,003 | 1/1963 | Blumenthal | 568/875 |
| 3,176,022 | 3/1965 | Blumenthal | 560/249 |
| 3,344,171 | 9/1967 | Lemberg | 568/875 |
| 3,433,839 | 3/1969 | Moroe et al. | 260/598 |
| 3,758,590 | 9/1973 | Bledsoe et al. | 252/522 R |
| 3,932,539 | 1/1976 | Kane et al. | 568/875 |
| 4,007,137 | 2/1977 | Sanders et al. | 252/522 R |

FOREIGN PATENT DOCUMENTS 2720839  11/1977  Fed. Rep. of Germany ........... 568/875

OTHER PUBLICATIONS

"Org. Reactions", Cope et al., Ed. vol. 11, pp. 322–330 (Chap. 5) John Wiley & Sons, New York, N.Y. (1964).
Takabe et al., "Bull. Soc. Chem. Jap", 46, 222–225 (1973).
Takabe et al., "Chem. Letters", pp. 1025–1026 (1977).

*Primary Examiner*—Norman Morgenstern
*Attorney, Agent, or Firm*—Robert F. Tavares; Thomas Cifelli, Jr.

[57] ABSTRACT

The instant invention provides a new and improved method of preparing the Diels Alder mixture of 3 and 4-(4-methyl-4-hydroxyamyl)$\Delta^3$-cyclohexenecarboxaldehyde from the readily available myrcene. The novel sequence includes a synthesis of a novel myrcenol, ocimenol intermediate which is substantially free of trans-ocimenol.

25 Claims, No Drawings

PROCESS FOR PREPARING A MYRCENOL, CIS-OCIMENOL MIXTURE SUBSTANTIALLY FREE OF TRANS-OCIMENOL

BACKGROUND OF THE INVENTION

The Diels-Alder adduct of myrcenol and acrolein is known in the art to consist of a mixture of I and II as illustrated below:

myrcenol   acrolein major I   minor II

When the reaction is uncatalysed (thermal) the ratio of I:II is about 3:1. In a catalysed reaction, I predominates even more and the ratio is more like 9:1. The art concerning the catalysed and uncatalysed reaction is provided in detail in U.S. Pat. No. 4,007,137.

The art also teaches processes to convert myrcene to myrcenol. In order to accomplish this, the diene portion of the myrcene must be protected before hydrating the isolated double bond. For example, U.S. Pat. No. 3,176,022 discloses a method wherein a cyclic sulfone is prepared by reacting myrcene with sulfur dioxide, the diene portion reacting with the sulfur dioxide in a Diels Alder type reaction. This myrcene sulfone was then hydrated and the resulting tertiary alcohol was heated to regenerate the diene and provide the desired myrcenol.

U.S. Pat. No. 3,932,539 teaches the preparation of a mixture of terpene alcohols consisting essentially of myrcenol and at least 20% cis-ocimenol and trans-ocimenol. According to this teaching, myrcene is hydrochlorinated to a mixture of linalyl chloride (ca. 10%), neryl and geranyl chlorides. These chlorides are reacted with a tertiary amine (trimethyl amine) to provide a quaternary ammonium salt which was then hydrated to form mixtures of cis and trans 3,7-dimethyl-7-hydroxy-2-octen-1-yl trimethyl ammonium chlorides. The chlorides are then converted to the hydroxides and thermally decomposed (Hofmann elimination) to provide a mixture of myrcenol, cis-ocimenol and trans-ocimenol.

Whereas a pure myrcenol was prepared via the sulfone intermediate (U.S. Pat. No. 3,176,022), the process utilizing the quaternary ammonium salt (U.S. Pat. No. 3,932,539) provided a mixture of myrcenol and ocimenols. Such a mixture of myrcenol, cis-ocimenol and trans-ocimenol is unsuitable for the preparation of Diels-Alder adducts such as 3 and 4-(4-methyl-4-hydroxyamyl)-$\Delta^3$-cyclohexanecarboxaldehyde since it is reported (U.S. Pat. No. 3,758,590) that ocimenol will react with acrolein to produce an adduct of its own.

It should be noted that while U.S. Pat. No. 3,758,590 does not appear to distinguish whether an adduct is formed from both cis-ocimenol and trans-ocimenol or only from one of these isomers, it is only the trans-ocimenol that is capable of forming an adduct with acrolein.

THE INVENTION

The present invention provides a novel and improved method of producing Diels-Alder adducts such as 3 and 4-(4-methyl-4-hydroxyamyl)$\Delta^3$-cyclohexanecarboxaldehyde from myrcenol derived from myrcene. The novel route is as follows:

SCHEME I myrcene geranyl amine myrcenol   cis-ocimenol

I   II   unreacted cis-ocimenol

In the above Scheme I the amine used is a secondary amine wherein $R_1$ and $R_2$ represent an ethyl or higher normal aliphatic group or, together, represent a cycloaliphatic group with an alkyl substituent on one of the carbons bonded to the nitrogen. $R_3$ is an alkyl group, suitably methyl through octyl, benzyl and the like. The X may be chlorine, bromine, iodine, methyl sulfate and the like. The anion, $X^-$, may also represent a hydroxide ion. The requirements for these substituents is discussed in more detail later in the specification.

The success of the above illustrated sequence depends on a number of surprising and unexpected discoveries. The importance of these discoveries to the success of the process is most clearly illustrated by considering, in reverse order, the novel sequence of steps as illustrated in Scheme I.

Step of Scheme I illustrates that when a mixture of myrcenol and cis-ocimenol is reacted with acrolein under Diels-Alder conditions, no adduct is formed from cis-ocimenol. It follows, therefore, that a mixture of myrcenol and cis-ocimenol provides a suitable starting material for the production of commercial mixtures of I and II since the unreacted cis-ocimenol can be easily separated by a distillation.

The critical step in the novel sequence is illustrated in step . It is the surprising and unexpected finding of this invention that the Hofmann elimination of an E-3,7-dimethyl-7-hydroxy-2-octen-1-yl trialkylammonium hydroxide (also referred to as the 7-hydroxygeranylamine quaternary hydroxide) proceeds to yield a mixture of myrcenol and cis-ocimenol which is substantially free of trans-ocimenol. The expression "substantially free of" is used herein to indicate that less than three percent of the material so designated is present in the product. The term "Hofmann Elimination" refers herein to the thermal decomposition of a quaternary ammonium hydroxide to provide an olefin. For a review see A. C. Cope and E. R. Trumbull, Organic Reactions, Vol. 11, p. 317, John Wiley and Sons, New York, 1960.

In contrast, if the Z-3,7-dimethyl-7-hydroxy-2-octen-1-yl trialkylammonium hydroxide (also referred to as the 7-hydroxy nerylamine quaternary hydroxide) is subjected to Hofmann elimination conditions, there is provided a product which is a mixture of trans-ocimenol and myrcenol wherein the trans-ocimenol is the major product. This mixture is substantially free of cis-ocimenol.

It follows that if the 3,7-dimethyl-7-hydroxy-2-octen-1-yl trialkylammonium hydroxide contains a significant portion of the Z-isomer, a Hofmann elimination could provide trans-ocimenol in an amount equivalent to about two-thirds of the Z-isomer. Any subsequent Diels-Alder reaction with acrolein would provide a product that was contaminated with the trans-ocimenol, acrolein adduct. It is desirable, therefore, to minimize the amount of the Z-isomer present in the 3,7-dimethyl-7-hydroxy-2-octen-1-yl trialkylammonium hydroxide in order to obtain a myrcenol, acrolein adduct that is substantially free of the trans-ocimenol, acrolein adduct.

Another surprising and unexpected finding of this invention is that the 1,4 addition of certain secondary amines to myrcene, as illustrated in step of Scheme I, can be controlled to provide a product which is predominantly the corresponding geranyl amine (E-isomer) with only minor amounts of the corresponding neryl amine (Z-isomer). Hereinafter the E-isomer (structure 2 in Scheme II below) will be referred to simply as the "geranyl amine" and the Z-isomer (structure 3 in Scheme II below) will be referred to simply as the "neryl amine".

The discoveries disclosed herein provide the perfumer with novel odorant compositions heretofore not available or, in some instances, not available in commercial quantities. These include:

(i) novel myrcenol, cis-ocimenol mixtures which are substantially free of trans-ocimenol;

(ii) a method for obtaining pure cis-ocimenol, which is considered in the perfume arts as more desirable than the trans-isomer; and (iii) novel trans-ocimenol, myrcenol mixtures which are substantially free of cis-ocimenol.

DESCRIPTION OF THE PREFERRED EMBODIMENTS

Scheme II illustrates the possible isomers that could result from a 1,4 addition of a secondary amine to myrcene. As mentioned, one of the objectives of this invention is to effect the course of the addition so that the material produced will be predominantly the "geranyl amine" (2) with only minor amounts of the "neryl amine" (3) or the iso-isomer (4) as impurities.

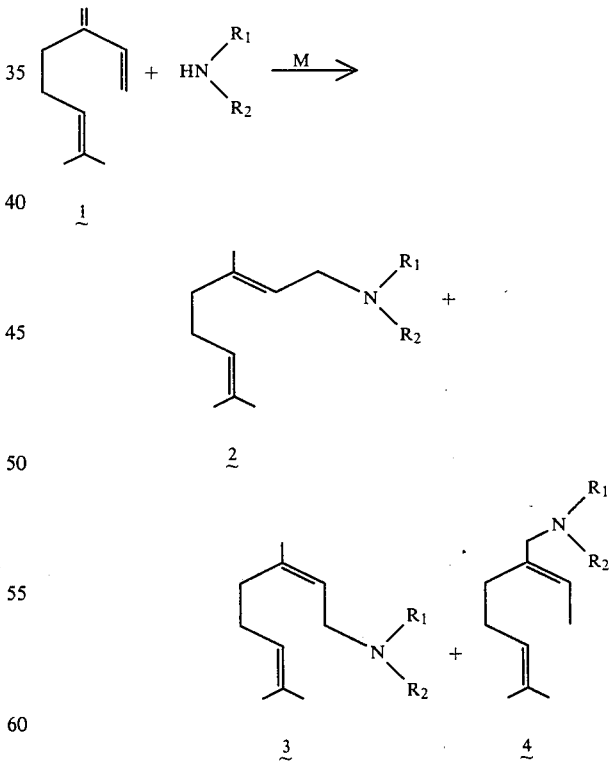

SCHEME II

Table I provides a number of examples of the reaction illustrated in Scheme II. This table clearly shows that the selectivity of the 1,4 addition of a secondary amine to myrcene depends on the nature of the amine and, to a lesser extent, on the metal.

TABLE I

The Reaction of Myrcene with Secondary Amines

| Example | Amine | Myrcene/ Amine Moles/ mole | Catalyst | Amine Catalyst Moles/ mole | Temp. | Time hours | Products 2 | 3 | 4 | Yield % |
|---|---|---|---|---|---|---|---|---|---|---|
| 1 | Et$_2$NH | 1.2 | BuLi | 28 | 25 | 72 | 96 | 2 | 2 | 87 |
| 2 | Bu$_2$NH | 1.25 | Li | 12 | 60 | 24 | 97 | 1 | 2 | 75 |
| 3 | Me$_2$NH | 1.5 | BuLi | 50 | 25 | 16 | 72 | 19 | 9 | 91 |
| 4 | Me$_2$NH | 1.1 | Na | 57 | 40–50 | 24 | 63 | 20 | 17 | 71 |
| 5 | Et$_2$NH | 1.2 | Na | 59 | 50 | 4 | 90 | 5 | 5 | 76 |
| 6 | Et$_2$NH | 1.6 | Na | 59 | 50 | 4 | 87 | 8 | 5 | 67 |
| 7 | Et$_2$NH | 2.0 | Na | 59 | 50 | 4 | 88 | 7 | 5 | 62 |
| 8 | iPr$_2$NH | 1.5 | BuLi | 12 | 60 | 30 | 95 | 4 | 1 | 26 |
| 9 | iPr$_2$NH | 1.5 | Na | 12 | 50 | 21 | 96 | 3 | 1 | 17 |
| 10 | Piperidine | 2.2 | BuLi | 20 | 60 | 18 | 69 | 21 | 10 | 64 |
| 11 | Bu$_2$NH | 1.25 | Na | 59 | 50 | 7 | 88 | 5 | 7 | 66 |
| 12 | * | 1.2 | BuLi | 20 | 50 | 28 | 97 | 0 | 3 | 85 |
| 13 | ** | 1.2 | BuLi | 10 | 60 | 96 | 97 | 2 | 1 | 47 |

*2-Methylpiperidine
**2,6-Dimethylpiperidine
a Yields based on amine

An examination of Table I shows that the addition of dimethyl amine is the least selective (examples 3 and 4), only about two thirds of the addition product being the desired "geranyl amine". Nearly 20% of the addition product is the unwanted "neryl amine" which would, after the subsequent transformations of Scheme I, be expected to result in a myrcenol, ocimenol mixture containing more than 10% of the undesirable trans-ocimenol.

It is therefore preferred to use diethyl amine or higher dialkyl secondary amines (examples 1, 2, 5–9, 11) which provide products in which the "geranyl amine" is about 90% and the "neryl amine" is less than 10%. While all such dialkyl amines provide the desired degree of selectivity, those dialkylamines wherein the alkyl group is a normal alkyl group (ethyl, n-propyl, n-butyl, etc.) are preferred over those wherein the alkyl group is a branched chain such as isopropyl etc. since the former result in higher yields.

Table I also shows that when cyclic secondary amines are used there must be a substituent α-to the nitrogen. When piperidine is used (example 10) the selectivity is about the same as when dimethylamine is used. In contrast, 2-methylpiperidine (example 12) and 2,6-dimethylpiperidine (example 13) provide high selectivity, the yield with the former being comparable to examples using diethylamine.

It was also found that the addition was somewhat more selective when the metal, M, was lithium rather than sodium. Table I shows that in examples employing diethylamine, those in which lithium was used (examples 1&2) provided about 95% of the "geranyl amine" with less than 5% of the "neryl amine" as compared with about 90% of the "geranyl amine" with less than 10% of the "neryl amine" when sodium was used (Examples 5,6&7).

In the preferred process of this invention a metal amide, MNR$_1$R$_2$ can be prepared by methods, known, or similar to those known, in the art. It is preferred the M be a sodium or lithium ion with lithium being especially preferred. It is also preferred that R$_1$ and R$_2$ be chosen from the group of ethyl, n-propyl, n-butyl or that R$_1$ and R$_2$ together represent the carbocyclic ring having a methyl group α to the nitrogen (e.g. 2-methyl-piperidine or 2,6-dimethylpiperidine). Diethylamine is the most readily available and economical of the above and is especially preferred.

Methods for preparing lithium or sodium amides from secondary amines are well known in the literature. Any of the known sources of active sodium or lithium may be used such as lithium metal, sodium metal, butyl lithium etc.

It is especially preferred to use lithium metal. The reaction of the lithium metal and the amine may be accelerated by the addition of a polycyclic aromatic compound such as naphthalene or biphenyl which forms a soluble charge transfer complex with the metal (Organometallic Compounds: Vol. I, 3rd Ed., G. E. Coates & K. Wade, Methuen, London 1967, page 59).

For each mole of amine to be used it is suitable to use 0.005–0.10 moles of lithium. It is preferred to use 0.01–0.05 moles of lithium per mole of amine with about 0.02 moles per mole being especially preferred.

It is preferred to add the metal or active metal compound (e.g. butyl lithium) to the amine. Although a solvent is not required, a suitable reaction-inert hydrocarbon solvent, such as hexane, benzene, toluene and the like may be used.

The myrcene is added to the amide, amine mixture. The reaction is exothermic. The temperature may be controlled by the rate of addition and/or external cooling. The reaction may be carried out at temperatures from about 0° C. to about 100° C. A reaction temperature of from 25° C. to 80° C. is preferred, with a temperature of about 60° C. being especially preferred.

The ratio of myrcene to amine is not critical. Preferred is a ratio of myrcene to amine of about 0.5 to 2.0 moles/mole, with a ratio of 0.8 to 1.2 being especially preferred.

Once the "geranyl amine" has been formed, the product may either be hydrated or alkylated in the next step as illustrated below (Scheme III). The order of the steps is not critical as the final product 7, is obtained by either method.

SCHEME III

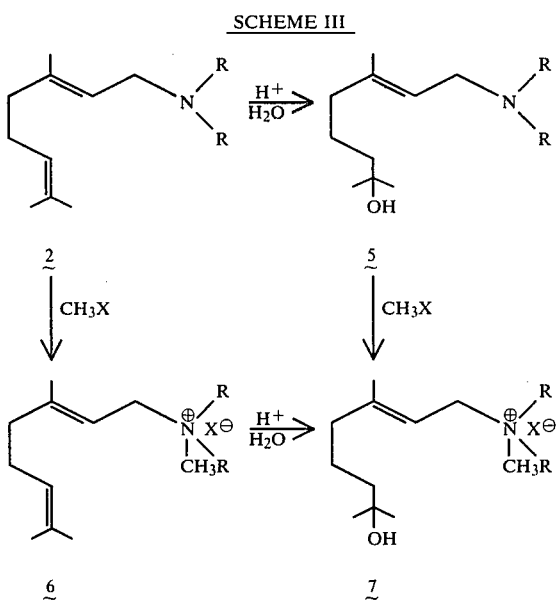

The hydration is accomplished with water in the presence of an acid. Water should be in excess of that required by the hydration but otherwise the amount is not critical. Any strong acid (e.g. one with pka <2) may be employed. Sulfuric, hydrochloric or phosphoric acids are preferred. Also suitable are strong organic acids such as benzenesulfonic, methanesulfonic acid or any strong organic acid which is part of a soluble or cross linked polymer. The strength of the acid may vary from 1–13 M, but is preferably 5–13 M. When the hydration of the amine is carried out, the amount of acid may be in the range 1.1–5.0 moles of acid per mole of amine but is preferably in the range 1.5–2.5 moles. For the hydration of the alkylated amine (quaternary ammonium salt) the amount of acid may be from 0.1 to 2.0 moles per mole of amine but is preferably in the range 0.1 to 1.0. It is preferred to carry out this hydration step at temperatures which are less than 50° C. but above 0° C.

The alkylation may be carried out by any standard procedure for preparing quaternary salts, using reagents such as any dialkyl sulfate ($R_2SO_4$) or alkyl halide RX, wherein X is Cl, Br or I. In Scheme III the alkyl group depicted is methyl, but other alkyl groups (e.g. methyl through octyl, benzyl and the like) are suitable. The simpler groups such as methyl or ethyl are preferred with methyl chloride or dimethyl sulfate being especially preferred alkylating agents primarily for reasons of economy and availability on a commercial scale.

For alkyl sulfates, a suitable temperature range is −50° C. to +50° C. while for alkyl chlorides a temperature range of +40° C. to 120° C. may be used. For benzyl chloride a suitable range is 0° to 100° C.

The salt is then converted to the hydroxide, a process which can be accomplished by any of the literature methods including the addition of an equivalent or more of a strong base such as sodium or potassium hydroxide. The preferred procedure is to add from 1 to 10 moles of sodium hydroxide, preferably as an aqueous solution from 1–30% by weight. The hydroxide is then subjected to the Hofmann elimination.

The salt 7 is converted to the hydroxide and then subjected to the Hofmann elimination. There are a number of methods for running the Hofmann elimination described in the literature and such methods are adaptable to this invention. For example methods by which the Hofman elimination may be applied to quaternary hydroxides similar to 7 is amply described in U.S. Pat. No. 3,932,539. We have determined that a suitable temperature range for the thermal decomposition is 60° to 140° C., with 80°–120° C. being preferred.

If the myrcenol, cis-ocimenol mixture so produced is reacted with acrolein, the myrcenol-acrolein adduct is formed and the cis-ocimenol remains unreacted. The unreacted cis-ocimenol can be separated from the adduct by distillation to provide a cis-ocimenol, essentially free of trans-ocimenol.

This invention also provides novel ocimenol, myrcenol mixtures. The "neryl amine", [which can be prepared according to K. Takabe et al, Tetrahedron Letters No. 39, pages 4009–12 (1972)], can be converted to novel mixtures comprising about 60–80% trans-ocimenol and about 20–40% myrcenol which are essentially free of cis-ocimenol.

Similarly, "geranyl amine" can be converted to novel mixtures comprising about 70–95% myrcenol and 30–5% cis-ocimenol.

ILLUSTRATION OF PREFERRED EMBODIMENTS

The following examples are included to illustrate the preferred embodiments of this invention and should not be construed as limiting. They are intended to embrace any equivalents or obvious extensions which are known or should be known to persons skilled in the art.

The first set of examples illustrate the preferred embodiments for preparing the "geranyl amines".

EXAMPLE 1

Preparation of N,N-diethylgeranylamine

Dry diethylamine (84 ml, 0.816 mole) was charged into a 500 ml 3 necked flask equipped with reflux condenser, thermometer, addition funnel and magnetic stirrer. The flask was swept out with dry nitrogen and maintained under a nitrogen blanket. Butyl lithium (16.6 ml, 2.2 M) in hexane was then added and the temperature raised to 50° C. After 15 minutes 200 ml 85% myrcene (1 mole) was added. The mixture exothermed and was cooled to 60°. After 4 hours at 60°, gas chromatography indicated that the amine had been converted to virtually a single product in high yield. Distillation gave a fraction boiling at 108° C./7 mm which was identified as diethylgeranylamine. The yield was 148.7 g (87% based on the amine used) of a product which was 96% "geranyl amine". (See Table I).

EXAMPLE 2

The process according to Example 1 was repeated using Di-n-butylamine (168.5 ml, 1 mole), 250 ml dry myrcene (1.25 moles), and 2 g of 30% lithium in oil as the lithium source. After reacting 17 hours at 60° C., a reaction product consisting of 97% N,N-dibutylgeranylamine, b.p. 108° C. (1 mm).

EXAMPLES 3–13

Examples 3 through 13 which were run in a manner similar to Examples 1 and 2 are summarized in Table I presented earlier.

EXAMPLE 14

Preparation of N,N-diethylgeranylamine

Into the dry reaction flask was charged 2.3 g of a lithium dispersion (30% in oil) and 10.0 g biphenyl. The flask was swept out with nitrogen. A serum cap was placed over one neck to facilitate samping with a syringe. Dry diethylamine 84.0 g (119 ml), was added and the mixture stirred for 1 hour to give an orange solution. Additional dry diethylamine, 318.0 g (450 ml), was then added followed by dry 85% myrcene, 801.5 g (1,000 ml). The reaction was exothermic and was maintained at ~60° with cooling initially. After 6½ hours the conversion was satisfactory (>95%). It can be checked by GC. When the conversion exceeds 95%, saturated sodium chloride solution (500 ml) and water (250 ml) was added. The mixture was then shaken in a separatory funnel and the layers separated. The organic layer was washed again with saturated sodium chloride solution (250 ml). The product was then distilled to give 893 g of N,N-diethylgeranylamine.

EXAMPLE 15

Preparation of 6,7-dihydro-7-hydroxygeranylamines

N,N-Diethylgeranylamine (627 g) was charged into a 3 liter flask. 940 g of 62.5% Sulfuric acid was added slowly with vigorous stirring keeping the temperature below 50° C. The reaction was allowed to stir overnight and then neutralized with 1600 g 30% caustic soda solution. The layers were separated. The aqueous phase was washed with 500 ml toluene. The organic phases were combined, washed with 500 ml of a 50% saturated brine solution, dried over MgSO₄, filtered and distilled to give 572.5 g of N,N-diethyl-(6,7-dihydro-7-hydroxygeranyl)amine boiling at 105°–107° C. @ 2 mm Hg. (84% yield)

EXAMPLE 16

Preparation of Myrcenol

Dimethylsulfate (126 g) was added slowly, over a 1 to 2 hour period, to 227 g N,N-diethyl-(6,7-dihydro-7-hydroxygeranylamine in 1000 ml toluene. The reaction was then stirred for another ½ hour. The two phases were then separated. The top phase was extracted 3 times with 200 ml portions of water and the aqueous extracts added to the bottom phase. The aqueous mixture was dripped slowly into 3000 ml of refluxing 30% sodium hydroxide solution and the product was collected by steam distillation. The steam distillate was washed sequentially with 100 ml 50% saturted brine, 100 ml 10% acetic acid, 100 ml water, 100 ml 10% sodium bicarbonate and 100 ml water. The product consisted approximately of 76.2% myrcenol, 23.8% cis-ocimenol with 2% or less of trans-ocimenol in an overall yield of 78.1%.

EXAMPLE 17

Myrcenol

Into a 300 ml autoclave was charged 60 g methanol and 113.5 g N,N-diethyl-(6,7-dihydro-7-hydroxygeranyl)amine. The reactor was further charged with 27 g methyl chloride and heated to 80° C. until finished (3-6 hrs). The reactor was cooled and vented and the residual methyl chloride removed under low vacuum.

The crude quaternary ammonium salt was charged into a steam distillation apparatus and 70 g of 30% sodium hydroxide was added. The mixture was steam distilled, maintaining a pot temperature of between 120° C. and 150° C. When no more organic material distilled, the distillate was extracted with 140 g hexane. The hexane solution was washed with 100 ml of a saturated aqueous sodium chloride solution. Vacuum distillation gave 66.1 g of a mixture of myrcenol (88.5%), cis-ocimenol (9.3%) and trans-ocimenol (2.2%).

EXAMPLE 18

Preparation of 3 and 4-(4-methyl-4-hydroxyamyl)Δ³-cyclohexenecarboxaldehyde

Into a pressure reaction vessel was charged 77 g of the myrcenol mixture from Example 17, 56 g acrolein and 1 g hydroquinone. The reactor was degased with nitrogen, stoppered and heated to 150° for four hours. Distillation of the resulting mixture gas 4-(4-methyl-4-hydroxyamyl)Δ³-cyclohexene carboxaldehyde together with the cis-ocimenol, which had not reacted.

EXAMPLE 19

Purification of cis-ocimenol

The cis-ocimenol recovered from Example 18 was purified further by reacting it with maleic anhydride, washing the reaction mixture with aqueous sodium hydroxide and distilling. This procedure resulted in cis-ocimenol that was at least 98% pure by vpc.

EXAMPLE 20

Preparation of N,N-Diethyl-(6,7-dihydro-7-hydroxyneryl)amine 105 g N,N-Diethylnerylamine was charged into a 500 ml 3 neck round bottom flask and stirred with a mechanical agitator. 157 g Of 62.5% sulfuric acid was added keeping the temperature below 10° C. After 3.5 hrs. a >95% conversion was observed and the reaction was quenched with 300 g 30% caustic soda. The reaction mixture was extracted 3×with 100 ml toluol, the toluol was back extracted with water and distilled to give 89.5 g N,N-diethyl-(6,7-dihydro-7-hydroxyneryl)amine boiling at 103°–105° C. @ 2 torr. for a 78% yield.

EXAMPLE 21

Preparation of trans-Ocimenol, Myrcenol Mixture

N,N-Diethyl-(6,7-dihydro-7-hydroxyneryl)amine was substituted for the N,N-diethyl-(6,7-dihydro-7-hydroxygeranyl)amine of Example 16. An 82% yield of a mixture of myrcenol (28.2%) and trans-ocimenol (71.8%) was obtained.

We claim:

1. A process for the preparation of a myrcenol, cis-ocimenol mixture, substantially free of trans-ocimenol, which comprises:

(a) preparing a geranyl amine of the formula:

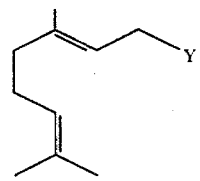

wherein:
Y represents

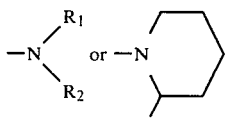

and R₁ and R₂ are alike or different and are chosen from the group consisting of ethyl, n-propyl and n-butyl;
by reacting myrcene with 2-methylpiperidine or a secondary dialiphatic amine of the formula:

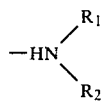

in the presence of its corresponding lithium amide;
(b) converting said geranyl amine to the corresponding E-3,7-dimethyl-2,6,-octadien-1-yl quaternary ammonium salt of the formula

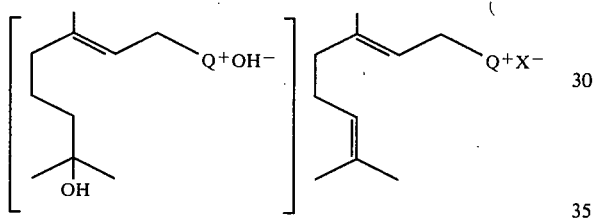

wherein:
X is Cl, Br, I or R₃SO₄;
Q represents

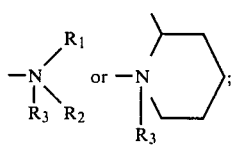

and R₃ is an alkyl group of one to eight carbons or a benzyl group;
(c) converting said quaternary ammonium salt to the corresponding E-3,7-dimethyl-7-hydroxy-2-octen-1-yl quaternary ammonium salt

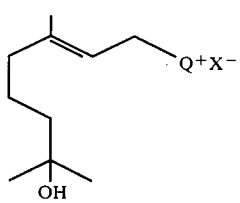

(d) converting said salt to the corresponding E-3,7-dimethyl-7-hydroxy-2-octen-1-yl quaternary ammonium hydroxide

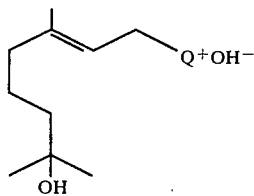

and
(e) subjecting said E-3,7-dimethyl-7-hydroxy-2-octen-1-yl quaternary ammonium hydroxide to Hofmann elimination conditions.

2. A process for the preparation of a myrcenol, cis-ocimenol mixture, substantially free of trans-ocimenol, which comprises:
(a) preparing a geranyl amine of the formula:

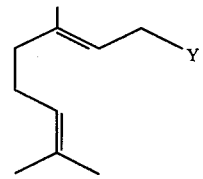

wherein:
Y represents

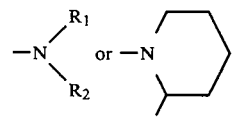

and R₁ and R₂ are alike or different and are chosen from the group consisting of ethyl, n-propyl and n-butyl;
by reacting myrcene with 2-methylpiperidine or a secondary dialiphatic amine of the formula:

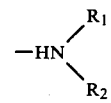

in the presence of its corresponding lithium amide;
(b) converting said geranyl amine to the corresponding 7-hydroxygeranyl amine

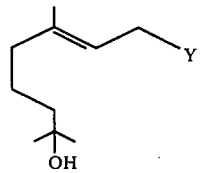

(c) converting said 7-hydroxygeranyl amine to the corresponding E-3,7-dimethyl-7-hydroxy-2-octen-1-yl quaternary ammonium salt

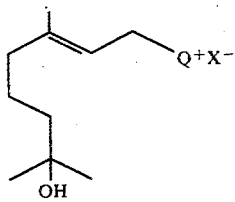

wherein:
X is Cl, Br, I or R₃SO₄;
Q represents

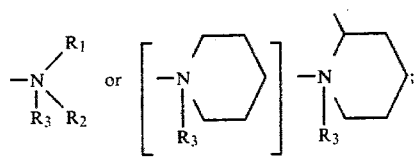

and R₃ is an alkyl group of one to eight carbons or a benzyl group;

(d) converting said salt to the corresponding E-3,7-dimethyl-7-hydroxy-2-octen-1-yl quaternary ammonium hydroxide of the formula

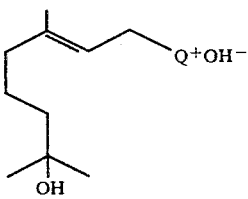

and
(e) subjecting said E-3,7-dimethyl-7-hydroxy-2-octen-1-yl quaternary ammonium hydroxide to Hofmann elimination conditions.

3. The process of claim 2 wherein:
(a) the geranyl amine

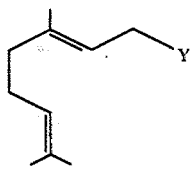

is converted to the corresponding 7-hydroxygeranyl amine

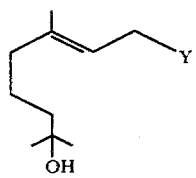

by reacting with:
(i) a 1–13 molar aqueous solution of a mineral acid selected from the group consisting of sulfuric, phosphoric and hydrochloric acids; or (ii) a 1–13 molar aqueous solution of an organic sulfonic acid of the formula R₄SO₃H wherein R₄ represents an alkyl group of from one to eight carbons, phenyl, tolyl or part of a soluble or cross linked polymer, and (b) the 7-hydroxygeranyl amine so produced is converted to

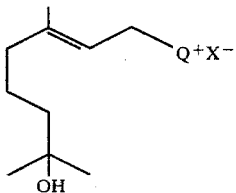

wherein X is Cl, Br, I or R₃SO₄; by reacting with the appropriate dialkyl sulfate, alkyl chloride, alkyl bromide, alkyl iodide, benzyl chloride, benzyl bromide or benzyl iodide.

4. The process of claim 1 wherein:
(a) the geranyl amine

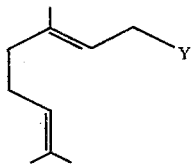

is converted to the corresponding E-3,7-dimethyl-2,6-octadien-1-yl quaternary ammonium salt of the formula

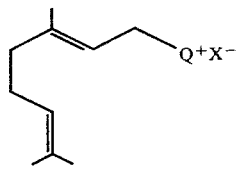

wherein X is Cl, Br, I or R₃SO₄; by reacting with dialkyl sulfate, alkyl chloride, alkyl bromide, alkyl iodide, benzyl chloride, benzyl bromide or benzyl iodide; and (b) the E-3,7-dimethyl-2,6-octadien-1-yl quaternary ammonium salt so produced is converted to

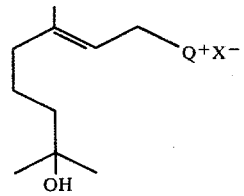

by reacting with
(i) a 1–13 molar aqueous solution of a mineral acid selected from the group consisting of sulfuric, phosphoric and hydrochloric acids; or
(ii) a 1–13 molar aqueous solution of an organic sulfonic acid of the formula R₄SO₃H wherein R₄ represents an alkyl group of from one to eight carbons, phenyl, tolyl or part of a soluble or cross linked polymer.

5. The process of claim 3 wherein
(a) the amine added to myrcene is diethylamine, dipropylamine, or α-methylpiperidine;
(b) the geranyl amine is reacted with a 1-13 molar mineral acid selected from the group consisting of sulfuric, phosphoric and hydrochloric acid at a temperature of from 0° C. to 50° C.; and
(c) the 7-hydroxygeranylamine is reacted with:
  (i) an alkyl halide selected from the group consisting of methyl through octyl chlorides, bromides or iodides at a temperature of from 40° C. to 120° C.; or
  (ii) a benzyl chloride, bromide or iodide at a temperature of 0° C. to 100° C.; or
  (iii) dimethylsulfate or diethylsulfate at a temperature of −50° C. to +50° C.

6. The process of claim 4 wherein
(a) the amine added to myrcene is diethylamine, dipropylamine or 2-methylpiperidine;
(b) the geranylamine is reacted with
  (i) an alkyl halide selected from the group consisting methyl through octyl chlorides, bromides or iodides at a temperature of from 40° C. to 120° C.; or
  (ii) a benzyl chloride, bromide or iodide at a temperature of from 0° C. to 100° C.; or
  (iii) dimethylsulfate or diethylsulfate at a temperature range of from −50° C. to +50° C.; and
(c) reacting the E-3,7-dimethyl-2,6-octadien-1-yl quaternary ammonium salt with a 1-13 molar mineral acid selected from the group consisting of sulfuric, phosphoric and hydrochloric acid at a temperature of from 0° C. to 50° C.

7. The process of claims 5 or 6 wherein the quaternary ammonium salt

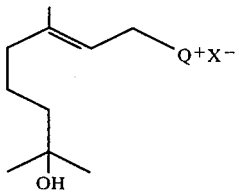

is added to from one to ten equivalents of sodium or potassium hydroxide at a temperature of from 60° C. to 140° C.

8. The process of claim 5 wherein
(a) lithium diethylamide is prepared by reacting 0.01 to 0.05 moles of lithium per mole of amine;
(b) there is added thereto from 0.8 to 1.2 molar equivalents of myrcene at a temperature of from 25° C. to 80° C. to provide N,N-diethylgeranylamine;
(c) the N,N-diethylgeranylamine so produced is reacted with 1.1 to 5.0 moles of 1.0 to 13.0 molar sulfuric acid per mole of amine at a temperature of from 0° C. to 50° C.;
(d) the 7-hydroxygeranylamine so produced is alkylated with methyl chloride at a temperature of from 40° C. to 120° C.;
(e) the 7-hydroxygeranyl diethylammonium chloride so produced is reacted with one to ten equivalents of sodium hydroxide; and
(f) the E-3,7-dimethyl-7-hydroxy, 2-octen-1-yl diethylammonium hydroxide so produced is heated to a temperature of from 60° C. to 140° C.

9. The process of claim 6 wherein
(a) lithium diethylamide is prepared by reacting 0.01 to 0.05 moles of lithium per mole of amine;
(b) there is added thereto from 0.8 to 1.2 molar equivalents of myrcene at a temperature of from 25° C. to 80° C. to provide N,N-diethylgeranylamine;
(c) the N,N-diethylgeranylamine so produced is alkylated with methyl chloride at a temperature of from 40° C. to 120° C.;
(d) the E-3,7-dimethyl-2,6-octadien-1-yl quaternary ammonium salt so produced is reacted with 0.1 to 2.0 moles of 1.0 to 13.0 molar sulfuric acid per mole of amine at a temperature of from 0° C. to 50° C.;
(e) the 7-hydroxygeranyl diethylammonium chloride so produced is reacted with one to ten equivalents of sodium hydroxide; and
(f) the E-3,7-dimethyl-7-hydroxy 2-octen-1-yl diethylammonium hydroxide so produced is heated to a temperature of from 60° C. to 140° C.

10. The process of claims 8 or 9 wherein the Hofmann elimination is done at from 80° C. to 120° C.

11. A process for the preparation of a trans-ocimenol, myrcenol mixture substantially free of cis-ocimenol which comprises
(a) converting a neryl amine of the formula

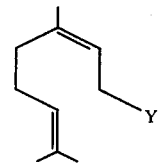

wherein:
Y represents

piperidyl or pyrrolidyl and
R₁ and R₂ are alike or different and are chosen from the group consisting of methyl, ethyl, n-propyl and n-butyl;
to the corresponding Z-3,7-dimethyl-2,6-octadien-1-yl quaternary ammonium salt of the formula

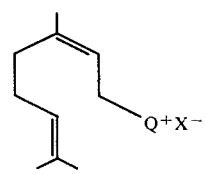

wherein:
X is Cl, Br, I or R₃SO₄;
Q represents

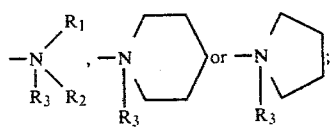

and R₃ is an alkyl group of one to eight carbons or a benzyl group;

(b) converting said salt to the corresponding Z-3,7-dimethyl-7-hydroxy-2-octen-1-yl quaternary ammonium salt

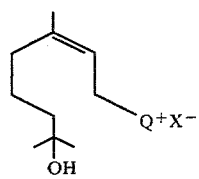

(c) converting said salt to the corresponding Z-3,7-dimethyl-7-hydroxy-2-octen-1-yl quaternary ammonium hydroxide

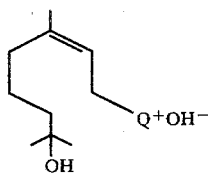

and (d) subjecting said Z-3,7-dimethyl-7-hydroxy-2-octen-1-yl quaternary ammonium hydroxide to Hofmann elimination conditions.

12. The process of claim 10 wherein Y is diethylamino or piperidyl.

13. The process of claim 12 wherein:
(a) the neryl amine

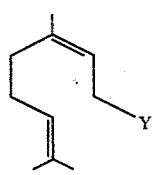

is converted to the corresponding Z-3,7-dimethyl-2,6-octadien-1-yl quaternary ammonium salt of the formula:

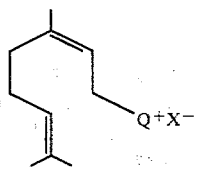

wherein X is Cl, Br, I or R₃SO₄ by reacting with dialkyl sulfate, alkyl chloride, alkyl bromide, alkyl iodide, benzyl chloride, benzyl bromide or benzyl iodide; and (b) the Z-3,7-dimethyl-2,6-octadien-1-yl quaternary ammonium salt so produced is converted to

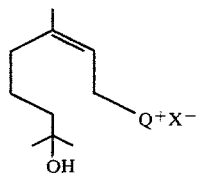

by reacting with
(i) a 1-13 molar aqueous solution of a mineral acid selected from the group consisting of sulfuric, phosphoric and hydrochloric acids, or
(ii) a 1-13 molar aqueous solution of an organic sulfonic acid of the formula R₄SO₃1+ wherein R₄ represents an alkyl group of from one to eight carbons, phenyl, tolyl or part of a soluble or cross linked polymer.

14. The process of claim 13 wherein:
(a) the neryl amine is reacted with
(i) an alkyl halide selected from the group consisting methyl through octyl chlorides, bromides or iodides at a temperature of from 40° C. to 120° C.; or
(ii) a benzyl chloride, bromide or iodide at a temperature of from 0° C. to 100° C.; or
(iii) dimethylsulfate or diethylsulfate at a temperature range of from −50° C. to +50° C.; and
(b) the E-3,7-dimethyl-2,6-octadien-1-yl quaternary ammonium salt so produced is reacted with a 1-13 molar mineral acid selected from the group consisting of sulfuric, phosphoric and hydrochloric acid at a temperature of from 0° C. to 50° C.;

15. The process of claim 14 wherein:
(a) N,N-diethyl neryl amine is alkylated with methyl chloride at a temperature of from 40° C. to 120° C.;
(b) the Z-3,7-dimethyl-2,6-octadien-1-yl quaternary ammonium salt so produced is reacted with 0.1 to 2.0 moles of 1.0 to 13.0 molar sulfuric acid per mole of amine at a temperature of from 0° C. to 50° C.;
(c) the 7-hydroxy neryl diethyl ammonium chloride so produced is reacted with one to ten equivalents of sodium hydroxide; and
(d) the E-3,7-dimethyl-7-hydroxy, 2-octen-1-yl, diethyl ammonium hydroxide so produced is heated to a temperature of from 60° C. to 140° C.

16. A process for the preparation of pure cis-ocimenol which comprises reacting a myrcenol, cis-ocimenol mixture which is substantially free of trans-ocimenol with acrolein or maleic anhydride in a Diels-Alder reaction and separating the unreacted cis-ocimenol from the Diels-Alder adduct.

17. The process of claim 16 wherein the myrcenol cis-ocimenol mixture is reacted with acrolein, and the cis-ocimenol recovered by distillation.

18. The process of claim 17 wherein the recovered cis-ocimenol is further purified by treating it with maleic anhydride under Diels-Alder conditions and separating the unreacted cis-ocimenol.

19. A process for the preparation of a trans-ocimenol, myrcenol mixture substantially free of cis-ocimenol which comprises
(a) converting a neryl amine of the formula

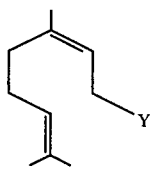

wherein:
Y represents

piperidyl or pyrrolidyl and
R₁ and R₂ are alike or different and are chosen from the group consisting of methyl ethyl, n-propyl and n-butyl;
to the corresponding 7-hydroxynerylamine

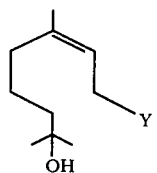

(b) converting said 7-hydroxynerylamine to the corresponding Z-3,7-dimethyl-7-hydroxy-2-octen-1-yl quaternary ammonium salt

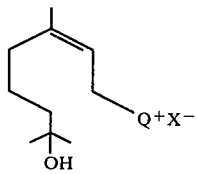

wherein:
X is Cl, Br, I or R₃SO₄;
Q represents

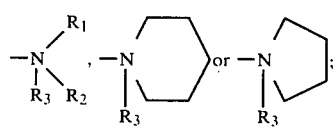

and R₃ is an alkyl group of one to eight carbons or a benzyl group; and
(c) converting said salt to the corresponding Z-3,7-dimethyl-7-hydroxy-2-octen-1-yl quaternary ammonium hydroxide of the formula

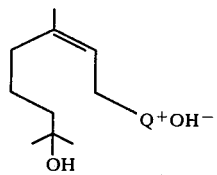

and
(d) subjecting said Z-3,7-dimethyl-7-hydroxy-2-octen-1-yl quaternary ammonium hydroxide to Hofmann elimination conditions.

20. The process of claim 19 wherein Y is diethylamino or piperidyl.

21. The process of claim 20 wherein:
(a) the neryl amine

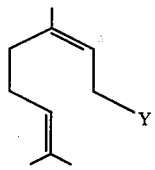

is converted to the corresponding 7-hydroxynerylamine

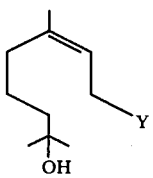

by reacting with:
(i) a 1–13 molar aqueous solution of a mineral acid selected from the group consisting of sulfuric, phosphoric and hydrochloric acids; or
(ii) a 1–13 molar aqueous solution of an organic sulfonic acid of the formula R₄SO₃H wherein R₄ represents an alkyl group of from one to eight carbons, phenyl, tolyl or part of a soluble or cross linked polymer; and
(b) the 7-hydroxynerylamine so produced is converted to

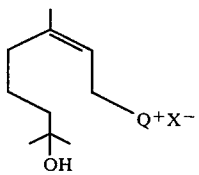

wherein X is Cl, Br, I or R₃SO₄; by reacting with the appropriate dialkyl sulfate, alkyl chloride, alkyl bromide, alkyl iodide, benzyl chloride, benzyl bromide or benzyl iodide.

22. The process of claim 21 wherein:
(a) the neryl amine is reacted with a 1–13 molar mineral acid selected from the group consisting of sulfuric, phosphoric and hydrochloric acid at a temperature of from 0° C. to 50° C.; and (b) the 7-hydroxy neryl amine so produced is reacted with (i) an alkyl halide selected from the group consisting of methyl through octyl chlorides, bromides or iodides at a temperature of from 40° C. to 120° C.; or (ii) a benzyl chloride, bromide or iodide at a temperature of 0° C. to 100° C.; or (iii) dimethyl sulfate or diethylsulfate at a temperature of −50° C. to +50° C.

23. The process of claims 22 or 14 wherein the quaternary ammonium salt

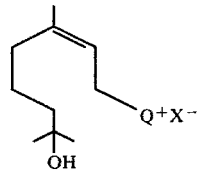

is added to from one to ten equivalents of sodium or potassium hydroxide at a temperature of from 60° C. to 140° C.

24. The process of claim 22 wherein
(a) N,N-diethyl neryl amine is reacted with 1.1 to 5.0 moles of 1.0 to 13.0 molar sulfuric acid per mole of amine at a temperature of from 0° C. to 50° C.;
(b) the 7-hydroxy neryl amine so produced is alkylated with methyl chloride at a temperature of from 40° C. to 120° C.;
(c) the 7-hydroxy neryl diethylammonium chloride so produced is reacted with one to ten equivalents of sodium hydroxide; and
(d) the Z-3,7-dimethyl-7-hydroxy, 2-octen-1-yl diethyl ammonium hydroxide so produced is heated to a temperature of from 60° C. to 140° C.

25. The process of claims 24 or 15 wherein the Hofmann elimination is done at from 80° C. to 120° C.

* * * * *